(12) United States Patent
Kazama et al.

(10) Patent No.: US 7,106,824 B2
(45) Date of Patent: Sep. 12, 2006

(54) X-RAY COMPUTED TOMOGRAPHIC APPARATUS

(75) Inventors: Masahiro Kazama, Sakura (JP);
 Shinsuke Tsukagoshi, Nasushiobara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/111,854

(22) Filed: Apr. 22, 2005

(65) Prior Publication Data
 US 2005/0249329 A1 Nov. 10, 2005

(30) Foreign Application Priority Data
 Apr. 26, 2004 (JP) .............................. 2004-129937

(51) Int. Cl.
 *A61B 6/00* (2006.01)
(52) U.S. Cl. ........................................ 378/16; 378/110
(58) Field of Classification Search .................. 378/16, 378/101, 108, 109, 110, 111, 112
 See application file for complete search history.

(56) References Cited

U.S. PATENT DOCUMENTS

2005/0228273 A1* 10/2005 Tamakoshi .................. 600/425

FOREIGN PATENT DOCUMENTS

JP  2004-329661  11/2004

* cited by examiner

*Primary Examiner*—Courtney Thomas
(74) *Attorney, Agent, or Firm*—Oblon, Spivak, McClelland, Maier & Neustadt, P.C.

(57) ABSTRACT

An X-ray computed tomographic apparatus includes an X-ray tube which generates X-rays, an X-ray detecting unit which detects X-rays transmitted through a subject to be examined to acquire projection data, an image reconstructing unit which reconstructs image data from the acquired projection data, and a tube current value setting unit which sets a tube current value for the X-ray tube on the basis of the projection data and information about contrast examination planned for the subject.

13 Claims, 8 Drawing Sheets

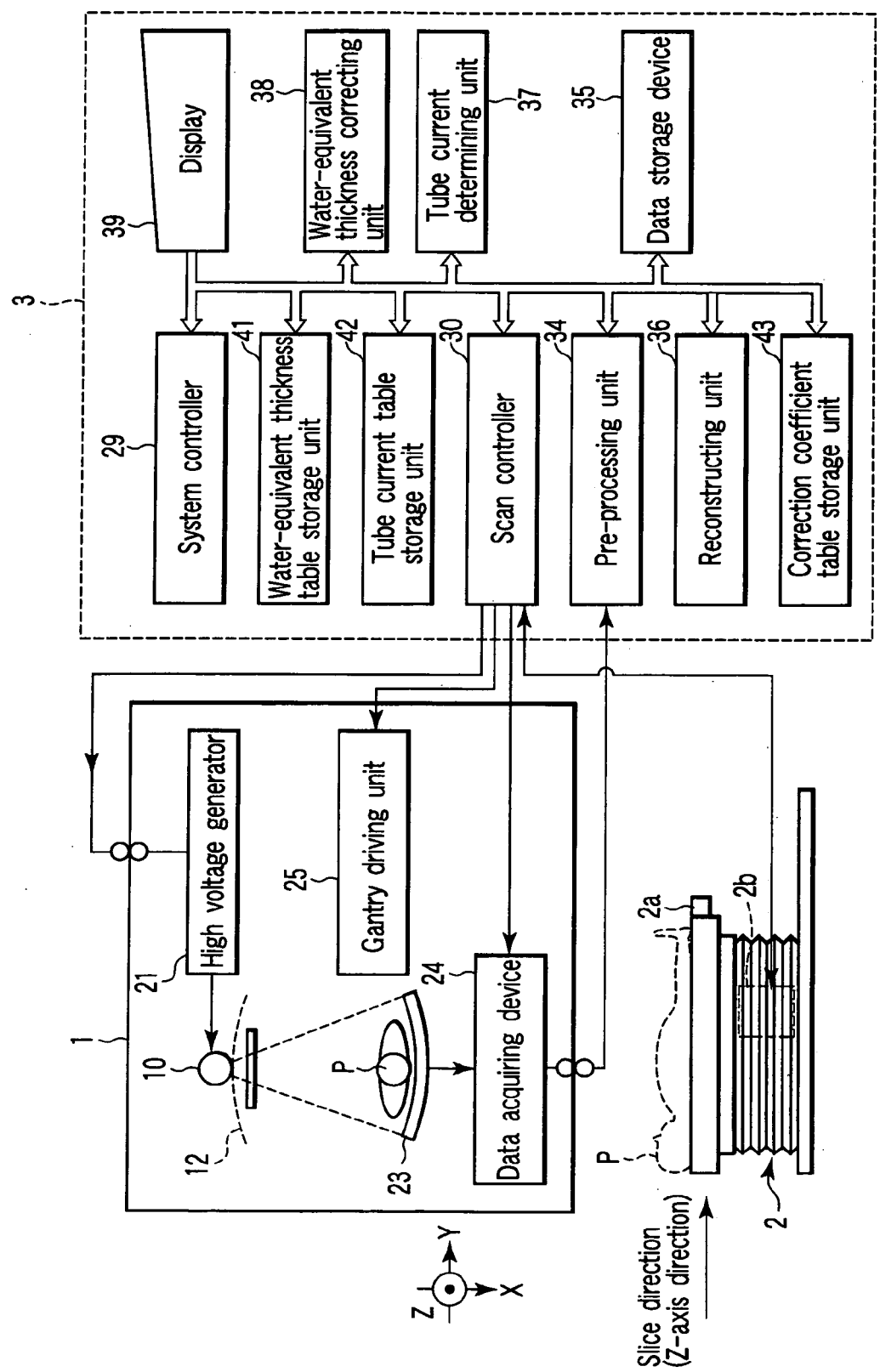
F I G. 1

| (Weight (Kg) × 2) − contrast medium amount (ml) | Coefficient A |
|---|---|
| −100 | 1.55 |
| −90 | 1.53 |
| −80 | 1.51 |
| −70 | 1.48 |
| −60 | 1.45 |
| −50 | 1.42 |
| −40 | 1.38 |
| −30 | 1.34 |
| −20 | 1.30 |
| −10 | 1.25 |
| 0 | 1.20 |
| 10 | 1.16 |
| 20 | 1.13 |
| 30 | 1.11 |
| 40 | 1.10 |
| 50 | 1.09 |
| 60 | 1.08 |
| 70 | 1.07 |
| 80 | 1.06 |
| 90 | 1.05 |
| 100 | 1.04 |

FIG. 2

| Contrast medium concentration (g/ml) | Coefficient B |
|---|---|
| 140 | 0.95 |
| 150 | 0.96 |
| 160 | 0.97 |
| 180 | 0.98 |
| 240 | 0.99 |
| 300 | 1.00 |
| 320 | 1.05 |
| 350 | 1.10 |
| 370 | 1.15 |
| 400 | 1.20 |

FIG. 3

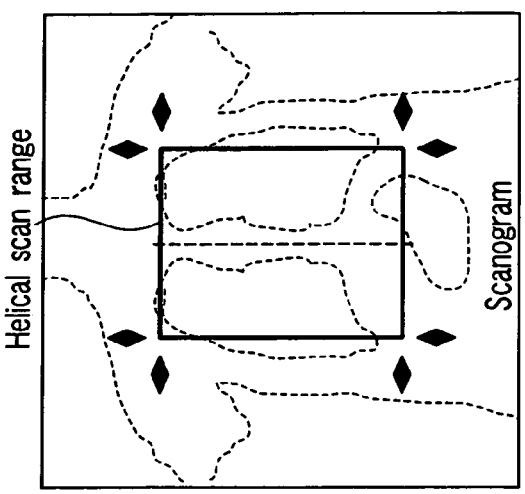
F I G. 5

X-RAY COMPUTED TOMOGRAPHIC APPARATUS

CROSS-REFERENCE TO RELATED APPLICATIONS

This application is based upon and claims the benefit of priority from the prior Japanese Patent Application No. 2004-129937, filed Apr. 26, 2004, the entire contents of both of which are incorporated herein by reference.

BACKGROUND OF THE INVENTION

1. Field of the Invention

The present invention relates to an X-ray computed tomographic apparatus.

2. Description of the Related Art

As is generally known, an X-ray computed tomographic apparatus is designed to obtain an image (tomographic image) by calculating (reconstructing) the X-ray absorption coefficient of a tissue such as an organ on the basis of the amount of X-rays absorbed in a subject to be examined as an index called a CT value with reference to the X-ray absorption coefficient of water.

A reconstructed image inevitably contains image noise. Image noise is typically defined with reference to a variation in the CT value of a homogeneous phantom image as a standard deviation, which is generally called an image SD. In order to make diagnosis by observing a reconstructed image, e.g., to discriminate a shadow on the image as noise or a tumor, the image SD unique to the image must be considered. For this purpose, as shown in FIG. 9, for example, the water-equivalent thickness of a subject to be examined is calculated from a scanogram taken in advance, and a tube current corresponding to a designated image SD is calculated from the water-equivalent thickness. In helical scan, as shown in FIGS. 10 and 11, tube currents are discretely calculated at intervals corresponding to a helical pitch along the body axis so as to maintain the designated image SD.

In contrast examination, however, since the X-ray absorption coefficient increases due to a contrast medium injected into the subject, the image SD increases, as shown in FIG. 11.

BRIEF SUMMARY OF THE INVENTION

It is an object of the present invention to provide an X-ray computed tomographic apparatus which can optimize a tube current in contrast examination, i.e., can suppress a change in image quality between non-contrast examination and contrast examination.

According to a first aspect of the present invention, there is provided an X-ray computed tomographic apparatus comprising an X-ray tube which generates X-rays, an X-ray detecting unit which detects X-rays transmitted through a subject to be examined to acquire projection data, and a tube current value setting unit which sets a tube current value for the X-ray tube on the basis of reconstruction of image data from the acquired projection data.

According to a second aspect of the present invention, there is provided an X-ray computed tomographic apparatus comprising an X-ray tube which generates X-rays, an X-ray detecting unit which detects X-rays transmitted through a subject to be examined to acquire projection data, and a tube current value setting unit which sets a tube current value for the X-ray tube on the basis of a planned injection amount of contrast medium with respect to the subject.

According to a third aspect of the present invention, there is provided an X-ray computed tomographic apparatus comprising an X-ray tube which generates X-rays, an X-ray detecting unit which detects X-rays transmitted through a subject to be examined to acquire projection data, and a tube current value setting unit which sets a tube current value for the X-ray tube on the basis of a planned contrast medium concentration with respect to the subject.

According to a fourth aspect of the present invention, there is provided an X-ray computed tomographic apparatus comprising a storage unit which stores projection data about a subject to be examined, and a tube current value setting unit which sets a tube current value for an X-ray tube on the basis of the projection data and information about contrast examination planned for the subject.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a view showing the arrangement of the main part of an X-ray computed tomographic apparatus according to an embodiment of the present invention;

FIG. 2 is a view showing an example of the first correction coefficient table stored in a correction coefficient table storage unit in FIG. 1;

FIG. 3 is a view showing an example of the second correction coefficient table stored in the correction coefficient table storage unit in FIG. 1;

FIG. 5 is a view showing an example of a scan plan window provided by a system controller in FIG. 1;

DETAILED DESCRIPTION OF THE INVENTION

Figure 4:
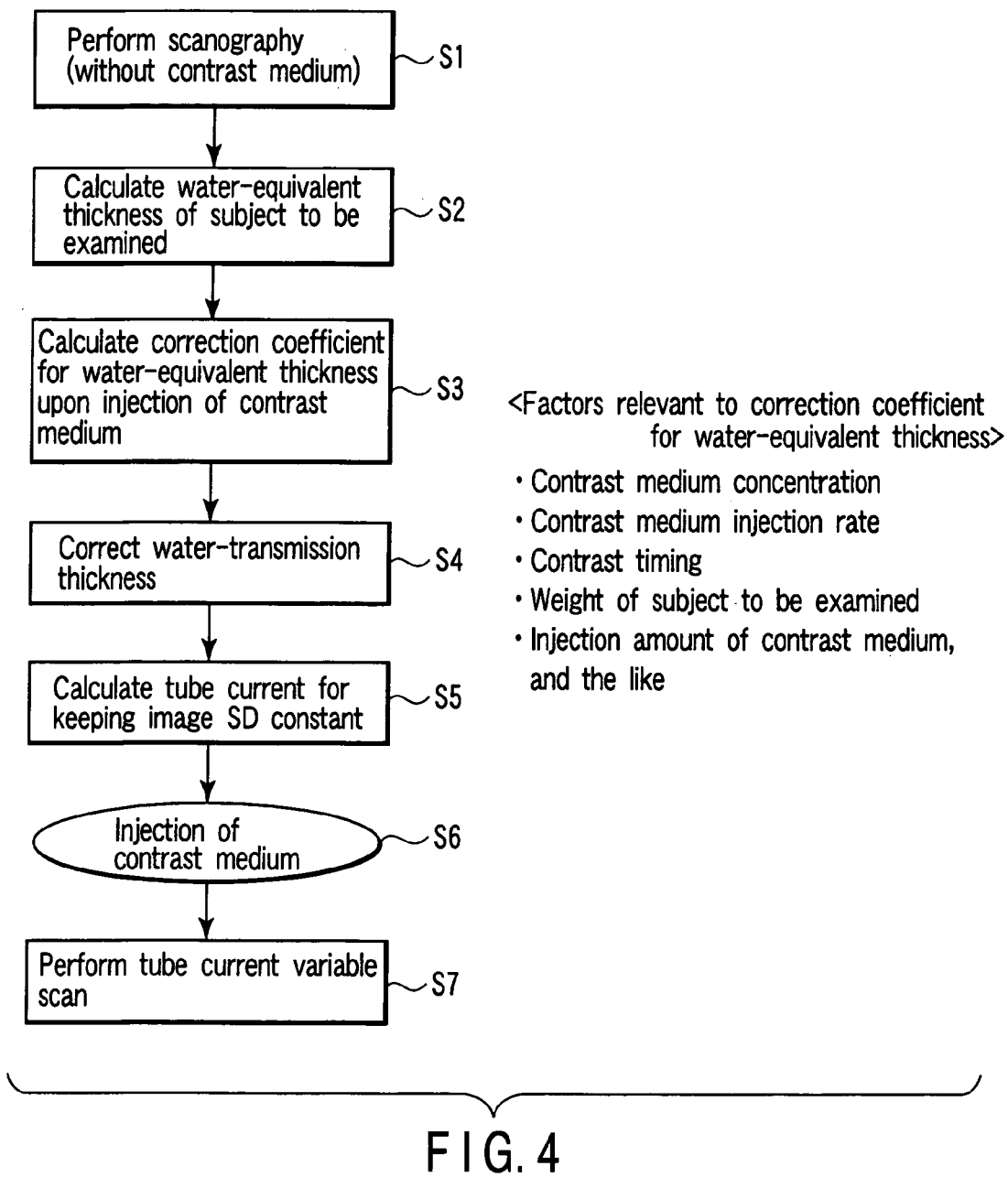
FIG. 4 is a flowchart showing a sequence for tube current determination processing by a tube current determining unit in FIG. 1.

An embodiment of an X-ray computed tomographic apparatus according to the present invention will be described below with reference to the views of the accompanying drawing. Note that X-ray computed tomography apparatuses include various types of apparatuses, e.g., a rotate/rotate-type apparatus in which an X-ray tube and X-ray detector rotate together around a subject to be examined, and a stationary/rotate-type apparatus in which many detection elements are arrayed in the form of a ring, and only an X-ray tube rotates around a subject to be examined. The present invention can be applied to either type. In this case, the rotate/rotate type, which is currently the mainstream, will be exemplified. In order to reconstruct one-slice tomographic image data, projection data corresponding to one rotation around a subject to be examined, i.e., about 360°, is required, or (180°+view angle) projection data is required in the half scan method. The present invention can be applied to either of these reconstruction schemes. The former scheme will be exemplified here. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used. In this case, the former type, i.e., the indirect conversion type, will be exemplified. Recently, with advances toward the commercialization of a so-called multi-tube type X-ray computed tomography apparatus having a plurality of pairs of X-ray tubes and X-ray detectors mounted on a rotating ring, related techniques have been developed. The present invention can be applied to both a conventional single-tube type X-ray computed tomography apparatus and a multi-tube type X-ray computed tomography apparatus. The single-tube type X-ray computed tomography apparatus will be exemplified here.

FIG. 1 shows the arrangement of an X-ray computed tomography apparatus according to this embodiment. This X-ray computed tomographic apparatus has a gantry 1 configured to acquire projection data about a subject to be examined in many directions. The gantry 1 has an X-ray tube 10 and X-ray detector 23. The X-ray tube 10 and X-ray detector 23 are mounted on an annular rotating frame 12. The rotating frame 12 is rotated about the Z-axis by a gantry driving device 25. An opening portion is formed in the central portion of the rotating frame 12. A subject P to be examined which is placed on a couch 2a of a couch 2 is inserted in the opening portion. The couch device 2 is equipped with a couch driving unit 2b for moving the couch 2a in the direction of the long axis (parallel to the rotation axis) of the couch. The couch driving unit 2b has a couch position detecting unit such as a rotary encoder for detecting the position of the couch 2a.

A high voltage generator 21 applies a tube voltage between the cathode and the anode of the X-ray tube 10. The high voltage generator 21 also supplies a filament current to the filament of the X-ray tube 10. X-rays are generated from the X-ray tube 10 by the application of the tube voltage and the supply of the filament current.

The X-ray detector 23 is a single slice type detector or multi-slice type detector. The X-ray detector 23 as a single slice type detector has an element array of, for example, 916 X-ray detection elements, each having a 0.5 mm×0.5 mm square light-receiving surface, arranged in a line along a channel direction Y. The X-ray detector 23 as a multi-slice type detector has, for example, 64 element arrays arranged side by side in the slice direction.

A data acquiring device 24 generally called a DAS (Data Acquisition System) converts a signal output from the X-ray detector 23 for each channel into a voltage signal, amplifies it, and further converts it into a digital signal. This data (raw data) is loaded into a computer unit 3 placed outside the gantry. A pre-processing unit 34 of the computer unit 3 performs correction processing such as sensitivity correction for the raw data output from a data acquiring device 26 and outputs the resultant projection data. This projection data is sent to a data storage device 35 of the computer unit 3 to be stored.

In addition to the pre-processing unit 34 and data storage device 35, the computer unit 3 is comprised of a system controller 29, an input device including a keyboard, mouse, and the like, a display 39, a scan controller 30, a reconstructing unit 36, a tube current determining unit 37, a water-equivalent thickness correcting unit 38, a display 39, a water-equivalent thickness table storage unit 41, a correction coefficient table storage unit 43, and a tube current table storage unit 42. The reconstructing unit 36 reconstructs tomographic image data from projection data by a reconstruction method selectively designated by the operator from a plurality of reconstruction methods. The plurality of reconstruction methods include, for example, as fan beam reconstruction methods (also called fan beam convolution/back projection methods) in which a projection ray obliquely crosses a reconstruction plane, the Feldkamp method as an approximate image reconstruction method in which a projection lay is regarded as a fan projection beam in convolution on the premise that the cone angle is small, and in which a reverse projection is processed along a scan ray, and a cone beam reconstruction method as a method which suppresses cone angle errors more than the Feldkamp method, in which projection data is corrected in accordance with the angle of a ray with respect to a reconstruction plane.

The water-equivalent thickness table storage unit 41 stores a table in which water-equivalent thicknesses are made to correspond to irradiation doses and transmission doses (the values of projection data of scanograms) at the time of scanography. Note that an irradiation dose and transmission dose represent X-ray absorption coefficients. A table may be prepared such that water-equivalent thicknesses are made to correspond to X-ray absorption coefficients. The correction coefficient table storage unit 43 stores a table in which correction coefficients for correcting a water-equivalent thickness in accordance with information about contrast examination are made to correspond to the information about contrast examination. The information about contrast examination includes the weights of subjects to be examined, the planned total injection amounts of contrast medium (contrast medium amounts: ml), the planned concentrations of contrast medium (g/ml), the planned amounts of contrast medium injected per unit time (e.g., 1 sec) (injection rates: ml/sec), delay times (contrast timings) between the injection of a contrast medium and the acquisition of projection data, and blood flow rates. In this case, the information about contrast examination is limited to the weights of subjects to be examined, the injection amounts of contrast medium (contrast medium amounts), and the concentrations of contrast medium injected into the subjects. In practice, the correction coefficient table storage unit 43 holds the first table shown in FIG. 2 and the second table shown in FIG. 3. In the first table, correction coefficients A are made to correspond to the values obtained by subtracting the contrast medium amounts from the weights (kg) twice those of the subjects. When, for example, a contrast medium of 100 ml is to be injected into a patient with a weight of 50 kg, the value "1.20" corresponding to index 0 (=50×2−100) is selected as the correction coefficient A. In the second table, correction coefficients B are made to correspond to contrast medium concentrations. A final correction coefficient is provided by correction coefficient A×correction coefficient B. Note that the first and second tables may be integrated into a single table. The single table is configured to output a correction coefficient (A×B) with respect to the input of the weight of a patient, the planned injection amount of contrast medium, and a contrast medium concentration.

The water-equivalent thickness correcting unit 38 acquires a water-equivalent thickness corresponding to the irradiation amount at the time of scanography and the data of a scanogram (the transmitted X-ray dose) from the water-equivalent thickness table storage unit 41. Water-equivalent thicknesses are discretely acquired at intervals equal to the helical pitch along the body axis of the subject.

The water-equivalent thickness correcting unit 38 acquires the correction coefficient A corresponding to the weight of the subject and the contrast medium amount and the correction coefficient B corresponding to the contrast medium concentration from the correction coefficient table storage unit 43. The water-equivalent thickness correcting unit 38 calculates a final correction coefficient by multiplying the correction coefficient A by the correction coefficient B. The water-equivalent thickness correcting unit 38 corrects the water-equivalent thickness acquired from the water-equivalent thickness table storage unit 41 by multiplying the water-equivalent thickness acquired from the water-equivalent thickness table storage unit 41 by the calculated final correction coefficient. This correction makes the water-equivalent thickness acquired from the water-equivalent thickness table storage unit 41 approximate the true water-equivalent thickness corresponding to the X-ray absorption coefficient of the subject which increases as a contrast medium is injected.

The tube current table storage unit 42 stores, for each of a plurality of image SDs, a table in which tube currents are made to correspond to water-equivalent thicknesses. When, for example, data acquisition is performed by using a tube current determined from a water-equivalent thickness in a table corresponding to a desired image SD, and a tomographic image is reconstructed, the tomographic image is obtained with an image SD in the table or image quality indicating an approximate value of the image SD. Desired image quality can be ensured. In other words, a change in image quality between non-contrast examination and contrast examination can be suppressed.

The tube current determining unit 37 acquires a tube current corresponding to the water-equivalent thickness corrected by the water-equivalent thickness correcting unit 38 and the image SD designated by the operator from the tube current table storage unit 42. In helical scan, water-equivalent thicknesses are discretely calculated at intervals corresponding to the helical pitch along the body axis of the subject, and tube currents are discretely determined at the intervals corresponding to the helical pitch along the body axis of the subject accordingly.

A tube current setting sequence according to this embodiment will be described next with reference to FIG. 4. First of all, scanography is performed in a non-contrast state (S1). As is generally known, scanography is performed by continuously applying X-rays to a subject to be examined and repeatedly detecting transmitted X-rays with the X-ray detector 23 while stopping the rotation of the X-ray tube 10 and X-ray detector 23 and moving the couch 2a at a constant speed. Scanogram data sent from the X-ray detector 23 through the data acquiring device 24 and pre-processing unit 34 are stored in the data acquiring device 35.

Although not shown, when the scanography is complete, the operator plans scan conditions on the scan planning window formed by the system controller 29 shown in FIG. 5 and a scan expert system (not shown) dedicated to scan planning. The scan conditions include items of helical scan/single scan (scan mode), helical scan range, single scan position, scan count, tube voltage (kV), tube current (mA), scan speed (rotational speed), reconstruction mode, diameter of imaging field of view (FOV), helical pitch, and the like. With regard to setting of a tube current (mA), this embodiment is provided with a mode of automatically controlling the tube current (mA) so as to maintain a designated image SD. For example, the operator clicks the tube current (mA) item to open a pull-down menu, and selects a desired tube current value from the pull-down menu or clicks "Auto". "Auto" corresponds to a start command for a function of automatically setting a tube current value to realize a designated image SD. When "Auto" is clicked, a submenu opens, which includes "High Quality", "Low Dose", and choices of a plurality of image SD values. When "High Quality", "Low Dose", or a desired image SD of the plurality of image SDs is selected, and the function of automatically setting a tube current is activated subsequently, the input boxes of "weight of subject to be examined", "contrast medium amount", and "contrast medium concentration" are added to the scan planning window in FIG. 5 under the control of the system controller 29.

Referring back to FIG. 4, when the scanography is complete and setting of scan planning is complete, the water-equivalent thickness correcting unit 38 acquires a water-equivalent thickness corresponding to an irradiation dose in the scanography and the data value of the scanogram (transmitted X-ray dose) from the water-equivalent thickness table storage unit 41 (S2). Water-equivalent thicknesses are discretely acquired at intervals equal to the helical pitch along the body axis of the subject. Note that a water-equivalent thickness may be calculated from the data value (transmitted X-ray dose) of a pixel of the scanogram which is located on the longitudinal central axis, or may be calculated from the average value (average transmitted X-ray dose) of a plurality of pixels of the scanogram which are located adjacent to each other. Alternatively, a water-equivalent thickness may be calculated from the average value (average transmitted X-ray dose) of a plurality of pixels of the scanogram which are located in a local area.

The water-equivalent thickness correcting unit 38 then acquires the correction coefficient A corresponding to the weight of the subject and a planned injection amount of contrast medium and the correction coefficient B corresponding to the planned concentration of contrast medium from the correction coefficient table storage unit 43. The water-equivalent thickness correcting unit 38 calculates a final correction coefficient by multiplying the correction coefficient B by the correction coefficient A (S3).

The water-equivalent thickness correcting unit 38 corrects the water-equivalent thickness acquired from the water-equivalent thickness table storage unit 41 by multiplying the water-equivalent thickness acquired from the water-equivalent thickness table storage unit 41 by the calculated final correction coefficient (S4). This correction can make the water-equivalent thickness acquired from the water-equivalent thickness table storage unit 41 approximate the true water-equivalent thickness corresponding to the X-ray absorption coefficient of the subject which increases as a contrast medium is injected.

Figure 6:
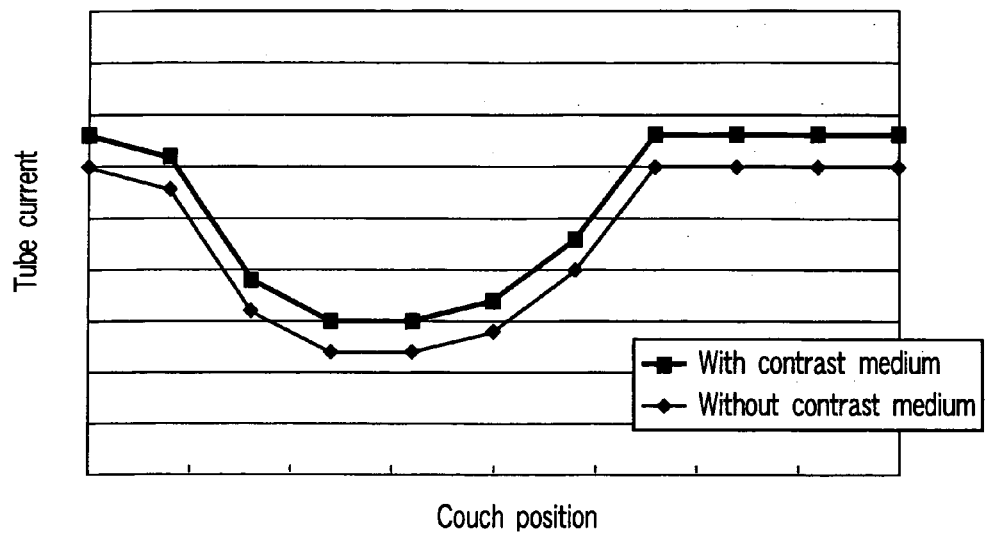
FIG. 6 is a view showing spatial changes in tube current corrected by the tube current determining unit in FIG. 1.
Figure 7:
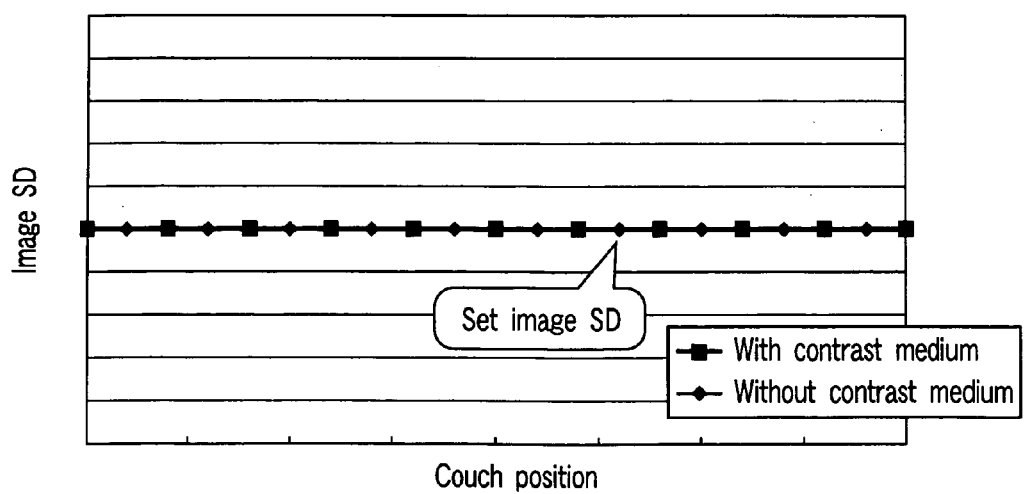
FIG. 7 is a view showing spatial changes in image SD due to tube currents corrected by the tube current determining unit in FIG. 1.

The tube current determining unit 37 then acquires a tube current corresponding to the water-equivalent thickness corrected by the water-equivalent thickness correcting unit 38 and the image SD designated by the operator from the tube current table storage unit 42 (S5). In helical scan, water-equivalent thicknesses are discretely calculated at intervals corresponding to the helical pitch along the body axis of the subject. Tube currents for keeping the image SD constant throughout the helical scan range are discretely determined at the intervals corresponding to the helical pitch along the body axis of the subject accordingly (see FIGS. 6 and 7).

Figure 8:
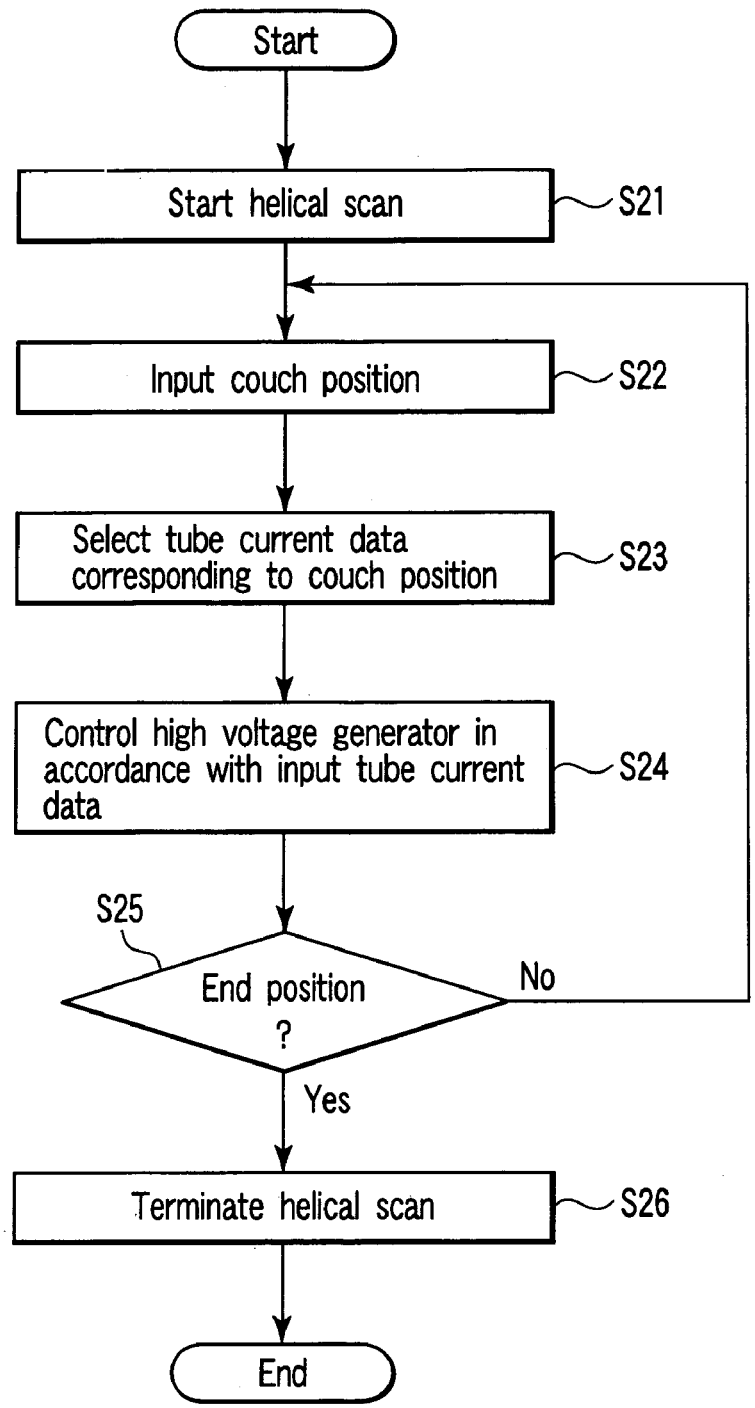
FIG. 8 is a flowchart showing a sequence for tube current control at the time of helical scan by a scan controller in FIG. 1.
Figure 9:
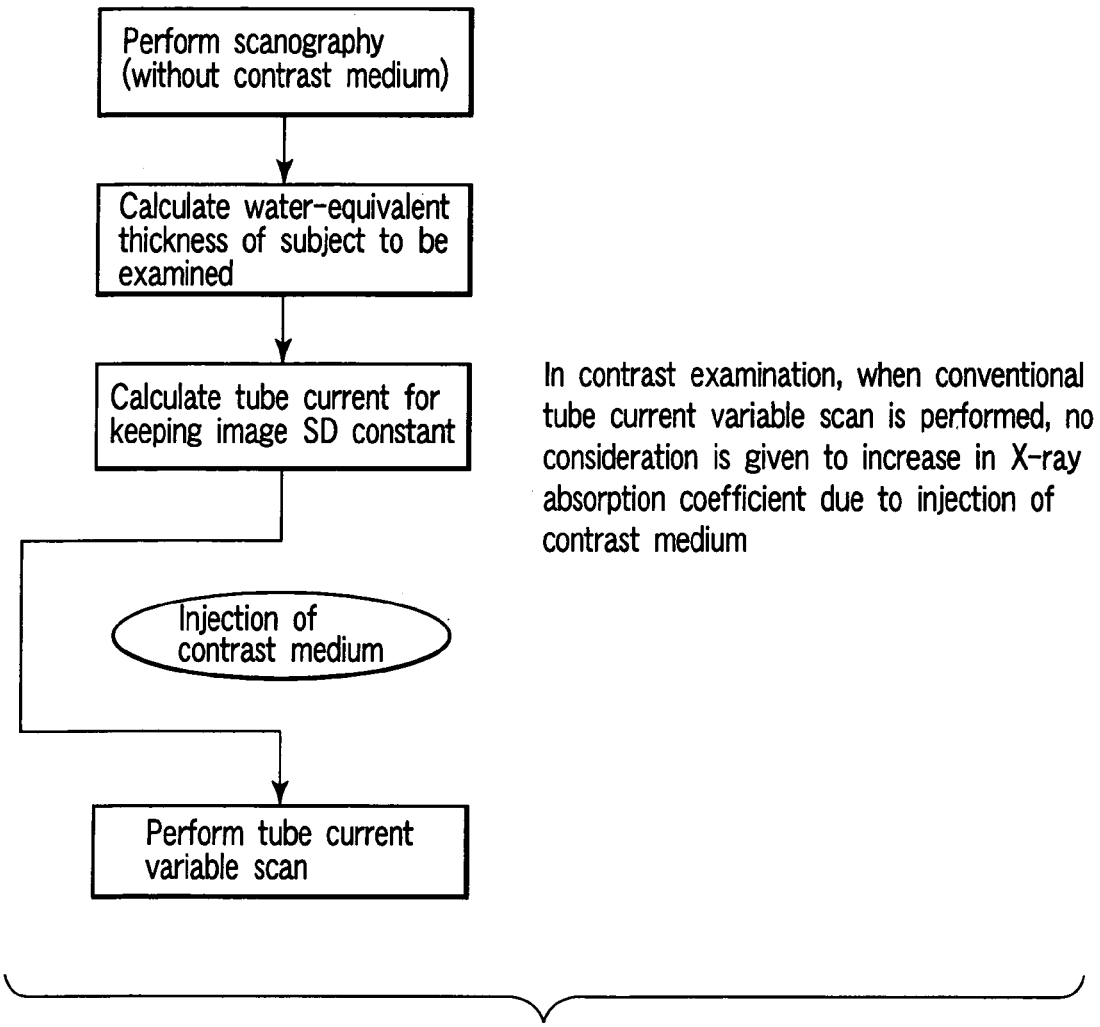
FIG. 9 is a flowchart showing a conventional sequence for tube current determination processing.
Figure 10:
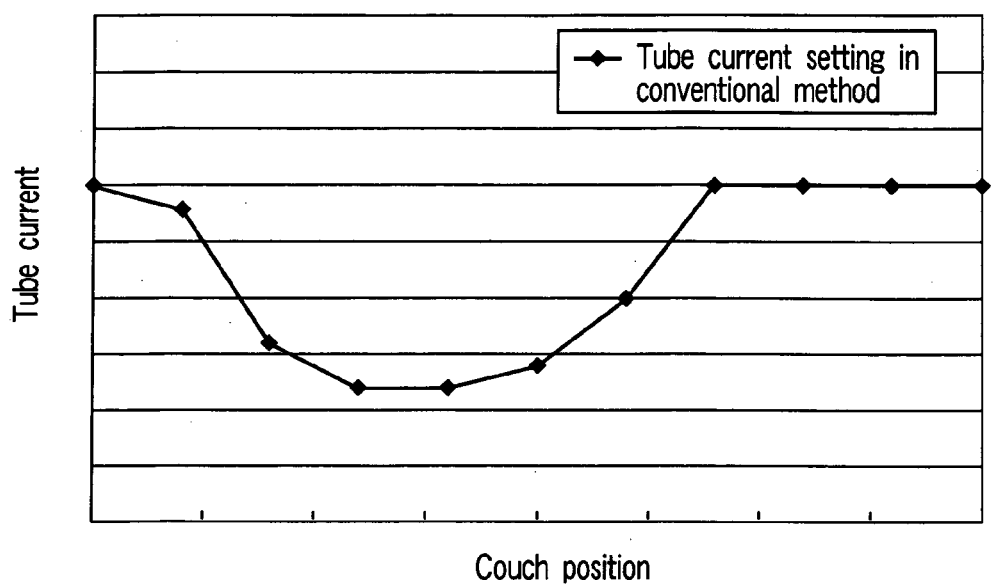
FIG. 10 is a view showing spatial changes in tube current determined by a conventional method.
Figure 11:
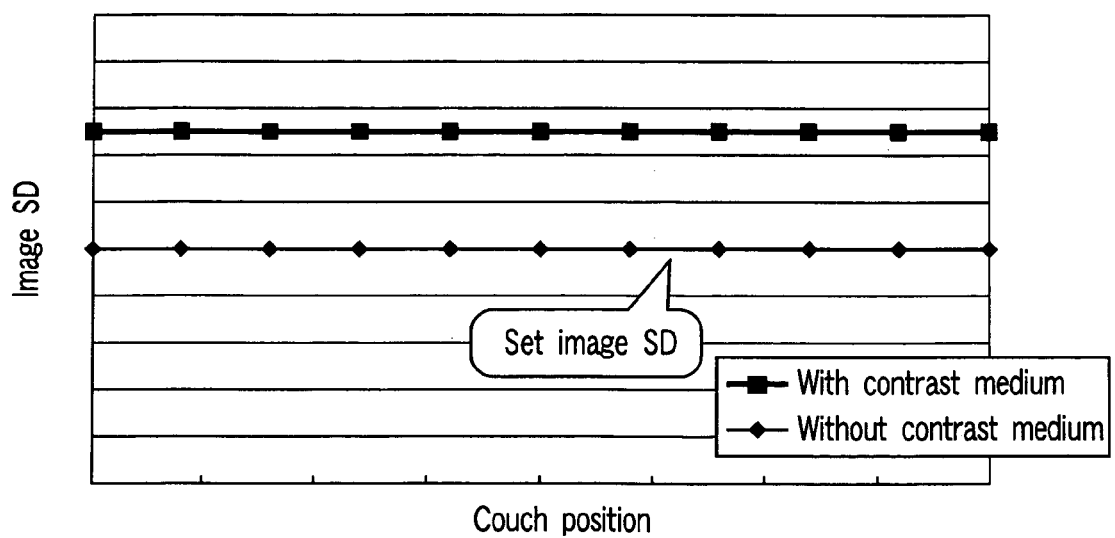
FIG. 11 is a view showing spatial changes in image SD due to tube currents determined by the conventional method.

When tube currents for keeping the image SD constant at a plurality of positions in the helical scan range are determined, a contrast medium is actually injected (S6), and tube current variable scan is executed to keep the image SD constant (S7). As shown in FIG. 8, when helical scan is started (S21), a couch position signal is supplied from the couch position detecting unit in the couch driving unit 2b of the couch 2 to the scan controller 30 as needed (S22). The scan controller 30 selectively reads out a tube current value corresponding to the couch position (S23), and controls the high voltage generator 21 in accordance with the tube current value. In practice, the scan controller 30 adjusts the filament current in the high voltage generator 21 so as to make the tube current in the X-ray tube 10 become equal to the selected tube current. The processing in S22 to S24 is continued until the couch position reaches the planned final position (S25). In this embodiment, since tube current values are determined at the respective discrete couch positions at the intervals corresponding to the helical pitch, a tube current is dynamically adjusted every time the X-ray tube 10 rotates once in synchronism with a rotation cycle during helical scan. Determining tube current values at the respective discrete couch positions at intervals shorter than the helical pitch makes it possible to finely adjust the tube current at intervals of, for example, 5° or 10° during one rotation.

As has been described above, according to this embodiment, even in contrast examination, the image quality (image SD) designated by the operator can be realized, and hence the operator can acquire an image with the planned image quality. This reduces the occasion of redoing scan and the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus, comprising:
   an X-ray tube configured to generate X-rays;
   an X-ray detecting unit configured to detect X-rays transmitted through a subject to be examined to acquire projection data;
   an image reconstructing unit configured to reconstruct image data from the acquired projection data; and
   a tube current value setting unit configured to set a tube current value for the X-ray tube on the basis of the projection data and information about contrast examination planned for the subjects,
   wherein the tube current value setting unit is configured to determine a water-equivalent thickness based on the projection data;
   the X-ray computed tomographic apparatus further includes a water-equivalent thickness correcting unit which corrects the determined water-equivalent thickness based on the information about the contrast examination; and
   the tube current value setting unit is configured to determine the tube current value based on the corrected water-equivalent thickness.

2. An X-ray computed tomographic apparatus according to claim 1, wherein the tube current value is determined to obtain the image data at an image quality level designated by the operator.

3. An X-ray computed tomographic apparatus according to claim 1, wherein the information about the contrast examination includes a weight of the subject, a planned injection amount of contrast medium in the subject, and a contrast medium concentration.

4. An X-ray computed tomographic apparatus according to claim 3, wherein the information about the contrast examination includes an injection rate of the contrast medium, and a delay time from injection of the contrast medium to acquisition of the projection data.

5. An X-ray computed tomographic apparatus according to claim 1, wherein the water-equivalent thickness correcting unit has a storage unit which stores a table in which a correction coefficient is made to correspond to the weight of the subject, the injection amount of contrast medium, and the contrast medium concentration which are contained in the information about the contrast examination, and a correcting unit which corrects water-equivalent thickness determined on the basis of a correction coefficient specified by the table.

6. An X-ray computed tomographic apparatus according to claim 1, wherein the tube current value setting unit sets the tube current value for obtaining a desired image quality level.

7. An X-ray computed tomographic apparatus according to claim 1, wherein a submenu for selecting the image quality level is provided under a menu for setting the tube current value.

8. An X-ray computed tomographic apparatus according to claim 1, wherein the tube current setting unit sets a tube current value for the contrast examination to a value different from a tube current value for non-contrast examination.

9. An X-ray computed tomographic apparatus according to claim 1, wherein the tube current value setting unit sets a plurality of tube current values with respect to a plurality of positions with respect to a body axis direction of the subject.

10. An X-ray computed tomographic apparatus according to claim 1, wherein the projection data used to set the tube current value originates from data of a scanogram associated with the subject.

11. An X-ray computed tomographic apparatus comprising:
    an X-ray tube configured to generate X-rays;
    an X-ray detecting unit configured to detect X-rays transmitted through a subject to be examined to acquire projection data;

an image reconstructing unit configured to reconstruct image data from the acquired projection data;

an inputting unit configured to input a desired value of an image standard deviation (SD) indicating an image quality; and a tube current value setting unit configured to set a tube current value for the X-ray tube on the basis of a water-equivalent thickness corresponding to the projection data, the desired value of the image SD, and a planned injection amount of contrast medium with respect to the subject.

12. An X-ray computed tomographic apparatus, comprising:

an X-ray tube configured to generate X-rays;

an X-ray detecting unit configured to detect X-rays transmitted through a subject to be examined to acquire projection data;

an image reconstructing unit configured to reconstruct image data from the acquired projection data;

an inputting unit configured to input a desired value of an image standard deviation (SD) indicating an image quality; and a tube current value setting unit configured to set a tube current value for the X-ray tube on the basis of a water-equivalent thickness corresponding to the projection data, the desired value of the image SD, and a planned contrast medium concentration with respect to the subject.

13. A tube current value setting device for an X-ray computed tomographic apparatus, comprising:

a storage unit configured to store projection data about a subject to be examined; and a tube current value setting unit configured to set a tube current value for an X-ray tube based on the projection data and an amount and a concentration of contrast medium planned for the subject.

* * * * *

UNITED STATES PATENT AND TRADEMARK OFFICE
CERTIFICATE OF CORRECTION

PATENT NO. : 7,106,824 B2 Page 1 of 1
APPLICATION NO. : 11/111854
DATED : September 12, 2006
INVENTOR(S) : Masahiro Kazama et al.

It is certified that error appears in the above-identified patent and that said Letters Patent is hereby corrected as shown below:

On the title page, Item (73) Assignee should read:

(73) Assignees: Kabushiki Kaisha Toshiba, Tokyo (JP)
Toshiba Medical Systems Corporation, Otawara-shi (JP)

Signed and Sealed this

Twenty-ninth Day of May, 2007

JON W. DUDAS
*Director of the United States Patent and Trademark Office*